United States Patent [19]

Tokinaga et al.

[11] Patent Number: 4,476,005
[45] Date of Patent: Oct. 9, 1984

[54] UREASE-IMMOBILIZED UREA ELECTRODE AND PROCESS FOR PREPARING THE SAME

[75] Inventors: Daizo Tokinaga; Teruaki Kobayashi, both of Hachioji; Akiko Katori, Koganei; Yoshiharu Karasawa, Tokyo, all of Japan

[73] Assignee: Hitachi, Ltd., Tokyo, Japan

[21] Appl. No.: 537,511

[22] Filed: Sep. 30, 1983

[30] Foreign Application Priority Data

Oct. 4, 1982 [JP] Japan ............................ 57-173226

[51] Int. Cl.³ ..................... G01N 27/30; C12Q 1/00; C12Q 1/58
[52] U.S. Cl. .................................. 204/403; 134/42; 435/12; 435/174; 435/177; 435/817
[58] Field of Search ............. 204/403, 1 E; 134/42; 435/12, 177, 174, 817

[56] References Cited

U.S. PATENT DOCUMENTS 3,776,819  12/1973  Williams .................. 204/403 X

OTHER PUBLICATIONS

G. G. Guilbault et al., Anal. Chem., vol. 45, No. 2, pp. 417–419, Feb. 1973.
M. Mascini et al., Anal. Chem., vol. 49, No. 6, pp. 795–798, May 1977.

Primary Examiner—G. L. Kaplan
Attorney, Agent, or Firm—Antonelli, Terry & Wands

[57] ABSTRACT

Urea electrode comprises a urease-immobilized membrane having added amino groups prepared by dipping an immobilized membrane in an aqueous solution of ethylenediamine or polylysine and an electrode for quantitative determination of ammonium ions. The electrode has a shorter measurement time with a larger electrode output.

9 Claims, 2 Drawing Figures

UREASE-IMMOBILIZED UREA ELECTRODE AND PROCESS FOR PREPARING THE SAME

BACKGROUND OF THE INVENTION

This invention relates to an enzyme electrode for measuring urea dissolved in a solution and to a process for preparing the same, and particularly to an enzyme electrode suitable for quantitative determination of urea in a short time and a process for preparing the same.

Enzyme electrode immobilized with an enzyme having a high reaction specificity to a substrate (test sample) and combined with an ion electrode, etc. were developed about ten years ago [G. G. Guilbault: Handbook of Enzymatic Method of Analysis, Marcel Dekker, New York (1976)], and some of such electrodes have been recently practically utilized, one of which is a urea electrode directed to urea as a test sample. Several types are available for the urea electrode, one of which uses urease as an enzyme and has such a structure that a urease-immobilized enzyme membrane is provided near an ammonium ion-selective electrode. However, a urea electrode of such type requires a long time in measuring one sample. This has been a problem.

SUMMARY OF THE INVENTION

The object of the present invention is to provide a urea electrode of said type, capable of measuring one sample in a shorter time and a process for preparing the same.

Structure of conventional urea electrode is schematically shown in FIG. 1, and the principle of measuring urea by such enzyme electrode will be briefly described below.

Urea contained in a sample solution 5 is decomposed by a urease-immobilized membrane 1 to form ammonium ions. The amount of the thus prepared ammonium ions is measured by an ammonium ion-selective electrode comprising an ammonium ion-sensitive membrane 2, an inner filling solution 3 and a silver-silver chloride electrode 4. Such an electrode is disclosed in, for example, Analytical Chem. 45-417-419(1973), etc.

In such an electrode, a measurement time depends upon permeabilities of urea and ammonium ions through a urease-immobilized membrane, and particularly largely upon the latter.

The present inventors have experimentally formed for the first time that, when urease-immobilized membranes are in the same structure, the permeability of ammonium ions largely depends upon the chemical properties of the structure of urease-immobilized membrane, and particularly the permeability of ammonium ions is higher with increasing amount of amino groups on the structure. Thus, the present inventors have found that in a urea electrode a measurement time can be shortened by introducing amino groups to the structure of urease-immobilized membrane.

The gist of the present invention is to use a urease-immobilized membrane with a high permeability of ammonium ions, and the present invention is applicable not only to an ammonium ion-selective electrode, but also to any electrode for directly or indirectly measuring ammonium ions. An example of such latter electrode is disclosed in Analytical Chem. 49-795-798(1977).

One embodiment of the present invention will be described in detail below, referring to the accompanying drawings.

PREFERRED EMBODIMENT OF THE INVENTION

Figure 1:
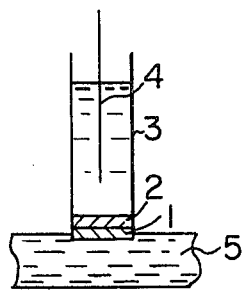
FIG. 1 is a schematic view of a structure of conventional urea electrode.
Figure 2:
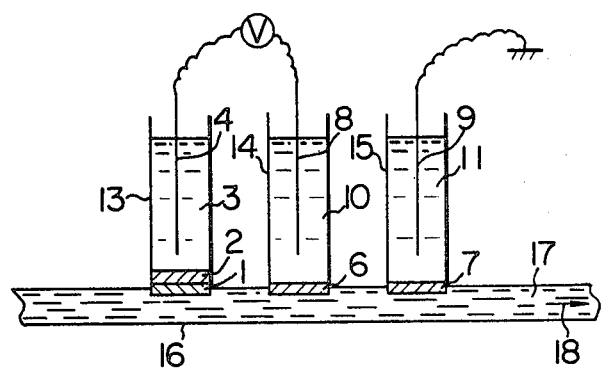
FIG. 2 is a schematic view of a urea electrode arrangement.

In FIG. 2, numeral 13 is an enzyme electrode, 14 a reference electrode, 15 an earthed electrode, 1 a urease-immobilized membrane, 2 an ammonium ion sensitive membrane, 6 and 7 dialysis membranes, 4, 8 and 9 silver-silver chloride electrodes, 3, 10 and 11 electrolyte solutions, 16 a conduit, 17 a buffer solution, and 18 an arrow mark showing the flow direction of buffer solution.

When a small amount (for example, 10 $\mu$l) of a sample, such as blood, etc. is passed through the conduit by using the buffer solution as a carrier, urea contained in the sample is hydrolyzed upon contact with the urease-immobilized enzyme 1 of enzyme electrode 13 to form ammonium ions. The ammonium ions change the membrane potential of ammonium ion-sensitive membrane 2, so that a potential change develops between the enzyme electrode 13 and the reference electrode 14, depending upon the urea concentration of the sample. The potential change can be observed as a peak change with time from the base line of single flow of buffer solution. The time from the start of peak change to returning to the base is taken as a measurement time of the sample.

Urease-immobilized membrane 1 for use in this embodiment is prepared by dissolving 40 mg of urease made by Boehringer Mannbeim GmbH, West Germany, and 80 mg of albumin (made by Seikagaku Kogyo Co., Ltd., Japan from bovine) in 1 ml of 0.2 M phosphate buffer solution (pH 7.4), adding 280 $\mu$l of an aqueous 2.5% glutaraldehyde solution thereto, extending the mixture on a glass flat plate, leaving it to stand thereon for at least 10 minutes for gelation and film formation, taking the thus formed film off the glass flat plate, and dipping the film in an aqueous 0.1–10% ethylenediamine solution neutralized with hydrochloric acid for 30 seconds to 10 minutes.

A urea electrode with the thus prepared urease-immobilized membrane can make measurement in an at least 10% shorter time with a 5–30% larger electrode output than a urea electrode with a urease-immobilized membrane without any dipping treatment with the aqueous diethylenediamine solution.

More specifically, as a result of dipping treatment with an aqueous 2% ethylenediamine solution for 10 minutes, a membrane having $10^{19}$ amino groups per 1 $cm^3$ of membrane volume can be obtained, whereas the untreated membrane has $10^{17}$ amino groups/$cm^3$ and takes 70 seconds for measurement of a sample at a urea nitrogen concentration of 100 mg/dl. The treated membrane takes 55 seconds for the same measurement with about 20% larger electrode output.

The said urease-immobilized gelated film is dipped in an aqueous polylysine solution in place of the said aqueous ethylenediamine solution to investigate its effect. Polylysine having different molecular weights are used for the test. It has been found that the same effect can be obtained with aqueous solutions of polylysine having a molecular weight of not more than 3,000 for the same short dipping time as with the aqueous ethylenediamine solution, and particularly preferably with polylysine having a molecular weight of not more than 1,000.

More specifically, as a result of dipping treatment with an aqueous 0.5% solution of polylysine having a molecular weight of 1,000 for 20 minutes, a urease-immobilized membrane having $10^{19}$ amino groups/cm$^3$ is obtained and takes 50 seconds for measurement of a sample at an urea nitrogen concentration of 100 mg/dl, which is considerably shorter than 70 seconds by the untreated membrane.

Urease-immobilized membranes having different numbers of amino groups obtained by changing the concentration of aqueous ethylenediamine solution and dipping time of urease-immobilized gelated membranes are used for test, and their characteristics as urea electrodes are investigated. As a result, it has been found that good characteristics are obtained with the membrane having at least $10^{18}$ amino groups/cm$^3$, particularly preferably with the membranes having at least $10^{19}$ amino groups.

The number of amino groups so far described is determined by dipping the membrane in a fluorescent isothiocyanate solution to effect fluorescent dyeing and by measuring the fluorescent intensity. Standard samples for the number of amino group are membranes prepared by thermo-setting aqueous albumin solutions having different concentrations and determined by subjecting the membranes to the same fluorescent dyeing. Quantitative determination of amino groups according to this method has an error of about ±20%, and it is difficult to obtain an exact absolute value, but the order of number can be exactly determined.

Larger number of amino groups is not objectionable, but its effect is not so improved over $10^{23}$, and thus it is preferably not more than $10^{23}$.

In the foregoing embodiment, ethylenediamine and polylysine have been mentioned, but other substances that have at least two amino groups in one molecule and can add the amino group throughout to the structure of urease-immobilized membrane, for example, guanidine, etc. can have the similar effect when used in the same manner as with ethylenediamine.

The same effect as above can be also obtained by dipping the untreated urease-immobilized enzyme after having assembled into a urea electrode in the said amine solution to give amino groups to the membrane.

According to the present invention, a measurement time of one sample can be shortened, and thus an increased number of samples can be measured in a unit time. Furthermore, according to the present invention, an electrode output can be increased, with an effect upon an increase in sensitivity.

What is claimed is:

1. A urea electrode comprising a urease-immobilized membrane and an electrode for quantitative determination of ammonium ions, the urease-immobilized membrane having added amino groups in the membrane structure.

2. A urea electrode according to claim 1, wherein the urease-immobilized membrane has at least $10^{18}$ amino groups per 1 cm$^3$ of membrane volume.

3. A urea electrode according to claim 1 or 2, wherein the urease-immobilized membrane is a membrane immobilized by glutaraldehyde.

4. A urea electrode according to claim 1, wherein the urease-immobilized membrane having added amino groups is a membrane prepared by dipping an urease-immobilized membrane in an aqueous solution of a compound having at least two amino groups in one molecule.

5. A urea electrode according to claim 4, wherein the compound is a compound having a molecular weight of not more than 3,000.

6. A urea electrode according to claim 5, wherein the compound is ethylenediamine, guanidine or polylysine.

7. A method for preparing a urease-immobilized membrane having added amino groups in the membrane structure for a urea electrode, which comprises dipping a urease-immobilized membrane in an aqueous solution of a compound having at least two amino groups in one molecule.

8. A method according to claim 7, wherein the compound is a compound having a molecular weight of not more than 3,000.

9. A method according to claim 8, wherein the compound is ethylenediamine or polylysine.

* * * * *